US008473202B2

(12) United States Patent  
Lapham

(10) Patent No.: US 8,473,202 B2
(45) Date of Patent: *Jun. 25, 2013

(54) AUTOMATION EQUIPMENT CONTROL SYSTEM

(75) Inventor: John R. Lapham, Fort Myers, FL (US)

(73) Assignee: C.H.I. Development Mgmt. Ltd. XXIV, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/244,085

(22) Filed: Sep. 23, 2011

(65) Prior Publication Data

US 2012/0016521 A1    Jan. 19, 2012

Related U.S. Application Data

(60) Division of application No. 11/190,145, filed on Jul. 26, 2005, now Pat. No. 8,050,797, which is a continuation of application No. 10/749,048, filed on Dec. 30, 2003, now Pat. No. 6,922,611, which is a continuation of application No. 10/227,660, filed on Aug. 26, 2002, now Pat. No. 6,675,070, which is a continuation-in-part of application No. 09/750,433, filed on Dec. 28, 2000, now Pat. No. 6,442,451.

(51) Int. Cl.
*G06F 7/00* (2006.01)

(52) U.S. Cl.
USPC ............. 701/445; 701/93; 701/117; 701/119; 701/29.2; 701/9; 455/404.2; 455/414.1; 455/418; 455/423; 455/440; 340/446; 340/539.13; 340/905; 340/995.13; 700/245; 700/248; 700/249; 700/251; 700/259; 318/568.1; 318/568.11; 318/568.15; 318/568.22

(58) Field of Classification Search
USPC ................ 701/93, 117, 119, 29.1, 29.2, 29.3, 701/201, 202, 210, 9, 10, 120, 445; 455/404.2, 455/414.1, 418, 423, 423.3, 426.1, 440, 440.1, 455/441, 453, 450, 456.1, 456.2, 456.3, 456.5, 455/457, 550.1, 517; 340/466, 539.13, 905, 340/995.13; 370/252; 342/357; 705/41; 700/245, 248, 249, 251, 259, 900; 318/318.1, 318/318.11, 318.15, 518.22

See application file for complete search history.

(56) References Cited

U.S. PATENT DOCUMENTS 4,218,757 A    8/1980   Drogichen
4,586,151 A    4/1986   Buote (Continued)

FOREIGN PATENT DOCUMENTS

EP    0007028    1/1980
EP    0180926    5/1986

(Continued)

OTHER PUBLICATIONS

Xuecai, Zhou et al. "A new robot control system with open architecture", Advanced Robotics, 1997. ICAR '97 Proceedings, 8th International Conference on Monterey, CA, USA Jul. 7-9, 1997, New York, NY, USA, IEEE, US, Jul. 7, 1997, pp. 813-818.

(Continued)

*Primary Examiner* — McDieunel Marc
(74) *Attorney, Agent, or Firm* — Perkins Coie LLP

(57) ABSTRACT

A automation equipment control system comprises a general purpose computer with a general purpose operating system in electronic communication with a real-time computer subsystem. The general purpose computer includes a program execution module to selectively start and stop processing of a program of equipment instructions and to generate a plurality of move commands. The real-time computer subsystem includes a move command data buffer for storing the plurality of move commands, a move module linked to the data buffer for sequentially processing the moves and calculating a required position for a mechanical joint. The real-time computer subsystem also includes a dynamic control algorithm in software communication with the move module to repeatedly calculate a required actuator activation signal from a joint position feedback signal.

19 Claims, 7 Drawing Sheets

U.S. PATENT DOCUMENTS

| | | | |
|---|---|---|---|
| 4,589,063 A | 5/1986 | Shah et al. | |
| 4,649,514 A | 3/1987 | Berger | |
| 4,689,755 A | 8/1987 | Buote | |
| 4,730,258 A | 3/1988 | Takeda et al. | |
| 4,831,549 A | 5/1989 | Red et al. | |
| 4,891,529 A | 1/1990 | Braun et al. | |
| 4,908,556 A | 3/1990 | Daggett et al. | |
| 4,954,762 A | 9/1990 | Miyake et al. | |
| 4,974,191 A | 11/1990 | Amirghodsi et al. | |
| 5,008,834 A | 4/1991 | Mizuno et al. | |
| 5,038,089 A | 8/1991 | Szakaly | |
| 5,113,346 A | 5/1992 | Orgun et al. | |
| 5,329,450 A | 7/1994 | Onishi | |
| 5,483,440 A | 1/1996 | Aono et al. | |
| 5,790,407 A | 8/1998 | Strickland et al. | |
| 5,825,981 A | 10/1998 | Matsuda | |
| 6,115,650 A | 9/2000 | Demarest et al. | |
| 6,219,032 B1 | 4/2001 | Rosenberg et al. | |
| 6,219,589 B1 | 4/2001 | Faraz et al. | |
| 6,233,504 B1 | 5/2001 | Das et al. | |
| 6,324,581 B1 | 11/2001 | Xu et al. | |
| 6,341,246 B1 | 1/2002 | Gerstenberger et al. | |
| 6,385,509 B2 | 5/2002 | Das et al. | |
| 6,424,885 B1 | 7/2002 | Niemeyer et al. | |
| 6,442,451 B1 * | 8/2002 | Lapham | 700/245 |
| 6,675,070 B2 * | 1/2004 | Lapham | 700/245 |
| 6,699,177 B1 | 3/2004 | Wang et al. | |
| 6,707,457 B1 | 3/2004 | Bates | |
| 6,837,883 B2 | 1/2005 | Moll et al. | |
| 6,839,612 B2 | 1/2005 | Sanchez et al. | |
| 6,922,611 B2 * | 7/2005 | Lapham | 700/245 |
| 6,950,731 B1 | 9/2005 | English | |
| 7,087,049 B2 | 8/2006 | Nowlin et al. | |
| 7,155,316 B2 | 12/2006 | Sutherland et al. | |
| 7,167,782 B2 | 1/2007 | Humbard et al. | |
| 8,050,797 B2 * | 11/2011 | Lapham | 700/245 |
| 2002/0111713 A1 | 8/2002 | Wang et al. | |
| 2003/0011493 A1 | 1/2003 | Wiplinger | |
| 2005/0182528 A1 | 8/2005 | Dwyer et al. | |
| 2006/0047365 A1 | 3/2006 | Ghodoussi et al. | |
| 2006/0178559 A1 | 8/2006 | Kumar et al. | |
| 2007/0032906 A1 | 2/2007 | Sutherland et al. | |
| 2012/0016521 A1 * | 1/2012 | Lapham | 700/258 |

FOREIGN PATENT DOCUMENTS

| | | |
|---|---|---|
| JP | 06055476 | 3/1994 |
| JP | 2009238233 | 10/2009 |
| WO | WO-9837466 | 8/1998 |
| WO | WO-9851456 | 11/1998 |
| WO | WO-02/054329 | 7/2002 |

OTHER PUBLICATIONS

Arda, Erol N. et al. "Open System Architecture Modular Tool Kit for Motion and Machining Process Control", IEEE/ASME Transactions on Mechatronics, IEEE Service Center, Piscataway, NJ, US, vol. 5, No. 3, Sep. 1, 2000, pp. 281-291.

State Intellectual Property Office, Notice of Allowance, Application No. 01821647.1, May 8, 2009, 3 pages.

European Patent Office, Supplementary Search Report, EP 01991483.7, Dec. 8, 2010, 4 pages.

International Search Report, International Application No. PCT/US01/49802, Jul. 11, 2002, 2 pages.

Preliminary International Examination Report, International Application No. PCT/US01/49802, May 26, 2003, 4 pages.

European Patent Office, Examination Report, EP 01991483.7, Mar. 28, 2011, 7 pages.

United States Patent and Trademark Office, Notice of Allowance, U.S. Appl. No. 09/750,433, mailed Jun. 20, 2002, 4 pages.

United States Patent and Trademark Office, Non-Final Office Action, U.S. Appl. No. 10/227,660, mailed Apr. 2, 2003, 8 pages.

United States Patent and Trademark Office, Non-Final Office Action, U.S. Appl. No. 10/227,660, mailed Jun. 26, 2003, 5 pages.

United States Patent and Trademark Office, Notice of Allowance, U.S. Appl. No. 10/227,660, mailed Aug. 1, 2003, 2 pages.

United States Patent and Trademark Office, Non-Final Office Action, U.S. Appl. No. 10/749,048, mailed Dec. 30, 2004, 4 pages.

United States Patent and Trademark Office, Notice of Allowance, U.S. Appl. No. 10/749,048, mailed Apr. 7, 2005, 2 pages.

United States Patent and Trademark Office, Non-Final Office Action, U.S. Appl. No. 11/190,145, mailed Apr. 18, 2007, 8 pages.

United States Patent and Trademark Office, Notice of Allowance, U.S. Appl. No. 11/190,145, mailed May 18, 2009, 9 pages.

United States Patent and Trademark Office, Non-Final Office Action, U.S. Appl. No. 11/190,145, mailed Sep. 29, 2009, 7 pages.

United States Patent and Trademark Office, Non-Final Office Action, U.S. Appl. No. 11/190,145, mailed Mar. 10, 2010, 10 pages.

United States Patent and Trademark Office, Non-Final Office Action, U.S. Appl. No. 11/190,145, mailed Nov. 22, 2010, 21 pages.

United States Patent and Trademark Office, Notice of Allowance, U.S. Appl. No. 11/190,145, mailed Jun. 27, 2011, 12 pages.

* cited by examiner

AUTOMATION EQUIPMENT CONTROL SYSTEM

CROSS-REFERENCE TO RELATED APPLICATIONS

This application is division of U.S. patent application Ser. No. 11/190,145, filed on Jul. 26, 2005, now U.S. Pat. No. 8,050,797, which is a continuation of U.S. patent application Ser. No. 10/749,048, filed on Dec. 30, 2003, now U.S. Pat. No. 6,922,611 which, in turn, is a continuation of U.S. patent application Ser. No. 10/227,660, filed on Aug. 26, 2002, now U.S. Pat. No. 6,675,070, which, in turn, is a continuation in part of U.S. patent application Ser. No. 09/750,433, filed on Dec. 28, 2000, now U.S. Pat. No. 6,442,451, all of which are incorporated by reference herein in their entireties.

FIELD OF THE INVENTION

This invention relates to an apparatus and method for controlling automation equipment and more particularly, to a versatile control system suitable for controlling automation equipment of various electro-mechanical configurations.

COPYRIGHT NOTIFICATION

Portions of this patent application contain materials that are subject to copyright protection. The copyright owner has no objection to the facsimile reproduction by anyone of the patent document, or the patent disclosure, as it appears in the Patent and Trademark Office.

BACKGROUND OF THE INVENTION

Industrial robots and similar highly flexible machine tools gained commercial acceptance during the late 1970s. Since then, the use of industrial robots has increased substantially, particularly for automobile manufacturing.

The guiding purpose for industrial robots is manufacturing flexibility. Robots allow assembly lines and work cells to make different articles with no or minimal manual equipment changes. The list of robot applications in manufacturing is long and ever increasing. Examples include computer vision inspection, spot and arc welding, spray painting, drilling, part placement, and adhesive application.

The boundary between robots and machine tools is not strictly defined, however. Compared with conventional machine tools, robots generally have more joints (or axes) of motion thereby offering more degrees of freedom for positioning an end effector. In the robotics field, the term "end effector" has been adopted to cover the variety of active equipment carried by robots. Such equipment varies according to the manufacturing application, e.g. spot welding.

Robots generally include positioning arms with mechanical joints, actuators such as motors for causing movement about the joints, and sensors which aid in determining the position (or pose) of the robot. Although most include these core components, industrial robots new and old otherwise vary greatly in their electromechanical configurations.

For example, some robots rely only on revolute, (i.e. rotary) joints, while some are equipped with combinations of linear and revolute axes. Robots with a series of extending arms and revolute joints have been labeled articulating robots.

Even among a given class of robots there is mechanical variation. The revolute joints of articulating robots may be, for example, offset from their supporting arm—a shoulder joint, centered to the supporting arm—an elbow joint or axially aligned with the supporting arm—a wrist joint. Likewise, linear joints may be co-linear or orthogonal. Actuators and feedback sensors are another source of the varying configurations. For example, some robots are equipped with stepper motors, others servo motors.

Electronic control systems are employed to control and program the actions of robots. For the necessary coordinated action between the end effector and the robot positioning, robot control systems preferably provide a level of software programming as well as an interface to field 110 and end effector subsystems. Conventional robot control systems are collections of customized electronics that vary according to robot configuration and robot manufacturer.

In manufacturing processes, robots are directed by a list of control instructions to move their respective end effectors through a series of points in the robot workspace. The sequences (or programs) of robot instructions are preferably maintained in a non-volatile storage system (e.g. a computer file on magnetic-disk).

Manufacturing companies, the robot users, through their engineers and technicians, have come to demand two important features from manufacturing control systems. First, robot users seek control systems implemented using commercially available standard computers and operating systems rather than customized proprietary systems. This trend toward the use of standard computer hardware and software has been labeled the "open systems movement."

Control systems based on standard computers are preferred because they offer robot users simplified access to manufacturing data via standard networks and I/O devices (e.g. standard floppy drives), the ability to run other software, and a competitive marketplace for replacement and expansion parts. Underlying the open systems movement is the goal of reducing robot users' long-term reliance on machine tool and robot manufacturers for system changes and maintenance.

A second feature sought by robot users is a common operator and programmer interface for all robots, facility (if not company) wide. A common user interface for all robots reduces the need for specialized operator training on how to use the customized proprietary systems.

With respect to the open-systems feature, efforts at delivering a robot control system based on standard, general purpose computer systems have not been fully successful because of the limitations of general purpose operating systems. Robot safety and accuracy requirements dictate that robot control systems be highly reliable, i.e. crash resistant, and tied to real-time. The multi-feature design objectives for general purpose operating systems such as Microsoft Windows NT® have yielded very complex, somewhat unreliable software platforms. Moreover, such systems cannot guarantee execution of control loops in real-time.

With respect to the common operator interface features, attempts to offer even limited standards to operator interfaces have not extended beyond a specific robot manufacturer. Notwithstanding the difficulty in getting different robot manufacturers to cooperate, the wide variety of electromechanical configurations has heretofore substantially blocked the development of robot control systems with a common operator interface.

Accordingly, it would be desirable to provide an improved robot control system that both employs standard computer systems and accommodates robots of different configurations. Specifically, it would be desirable to provide the advantages of open systems and a common operator interface to robot control.

SUMMARY OF THE INVENTION

Robot control systems of the present invention provide robot control via commercially standard, general purpose computer hardware and software. The control systems and methods according to the present invention are usable with robots of varying electromechanical configurations, thereby allowing a common operator interface for robots from different robot manufacturers.

The present invention provides a control system for running or processing a program of robot instructions for robots equipped with a mechanical joint, a mechanical actuator to move the joint and a position feedback sensor. The robot mechanical actuators receive an activation signal and the feedback sensor provides a position signal.

A control system embodying the present invention includes a general purpose computer with a general purpose operating system and a real-time computer subsystem in electronic communication with the general purpose computer and operably linked to the mechanical actuator and the position feedback sensor. The general purpose computer includes a program execution module to selectively start and stop processing of the program of robot instructions and to generate a plurality of robot move commands.

Within the real-time computer subsystem is a move command data buffer for storing a plurality of move commands. The real-time computer subsystem also includes a robot move module and a control algorithm. The move module is linked to the data buffer to sequentially process the move commands and calculate a required position for the mechanical joint. The control algorithm is in software communication with the robot move module to repeatedly calculate a required activation signal from the feedback signal and the required position for the mechanical joint.

Another aspect of the present invention provides a robot control system suitable for controlling robots of different electromechanical configurations. The control system includes a robot-independent computer unit in electronic and software communications with a robot-specific controller unit.

The robot-independent computer unit is operably linked to the robot by an I/O interface and includes a video display and a first digital processor running an operator interface module for creating a sequence of robot move commands. The robot-specific controller unit includes a second digital processor running a real-time tied operating system and a robot move module for executing the robot move commands.

The operator interface module preferably includes a configuration variable for storing data defining the electromechanical configuration of the robot, a first code segment for generating a first operator display according to a first electromechanical configuration, a second code segment for generating a second operator display according to a second electromechanical configuration, and a third code segment for selecting the first or second code segment according to the electromechanical configuration.

Control systems according to the present invention are well suited for use with various types of automation equipment having actuator-driven mechanical joints. The automation equipment category includes, but is not limited to, robots, machine tools, laboratory liquid-handling systems, computer media handling systems, therapeutic systems, surgical systems, and the like.

In this aspect, the present invention provides a control system for processing a program of instructions for automation equipment having a mechanical joint, a mechanical actuator to move the joint and a position feedback sensor. The mechanical actuator is set up to receive an activation signal and the feedback sensor is set up to provide an indication of the joint's position. The equipment control system comprises a general purpose computer with a general purpose operating system and a real-time computer subsystem operably linked to the mechanical actuator and the position feedback sensor. The real-time computer subsystem is in electronic communication with the general purpose computer, preferably via a standard data bus.

The general purpose computer includes a program execution module to selectively start and stop processing of the program of instructions for the automation equipment and to generate a plurality of corresponding move commands. The real-time computer subsystem has a move command data buffer for storing the plurality of move commands, a move module linked to the data buffer to sequentially process the plurality of move commands and calculate a required position for the mechanical joint of the automation equipment.

Yet another aspect of the present invention is the capability to simultaneously control multiple such automation devices. According to this aspect, the present invention provides a control system suitable for controlling a plurality of automation devices with mechanical joints and mechanical actuators to move the respective joints. The control system comprising a general purpose computer with a general purpose operating system and a plurality of real-time computer subsystems each in electronic communication with the general purpose computer.

The general purpose computer includes a video display and a first digital processor adapted to run an operator interface, which serves to create a sequence of device move commands. Each real-time computer subsystem is operably linked to one of the automation devices. Each subsystem has a digital processor adapted to run a real-time tied operating system and a move module for executing the move commands.

Other advantages and features of this invention will be readily apparent from the following detailed description of the preferred embodiment of the invention, the drawings, and the appended claims.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
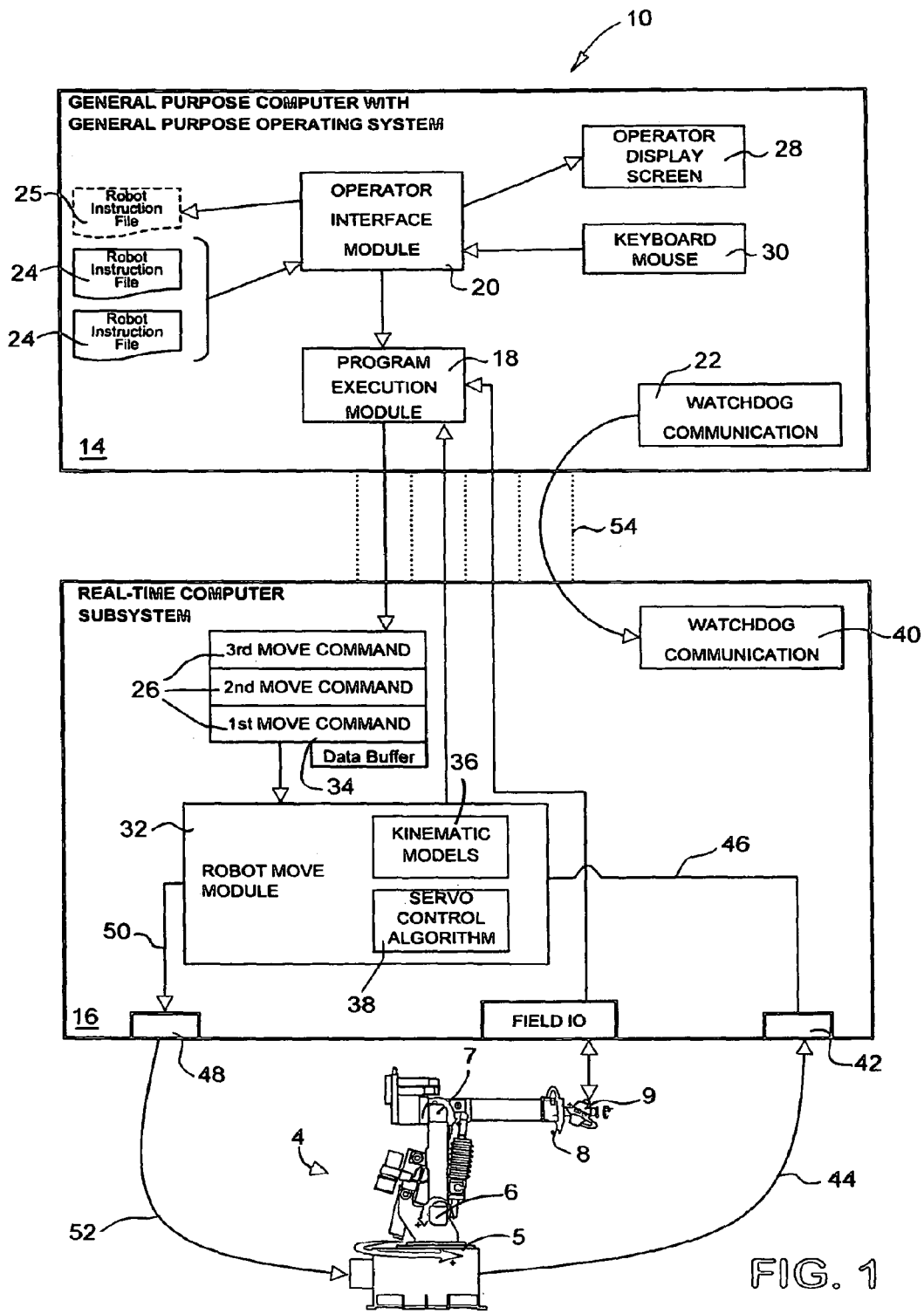
FIG. 1 is schematic block diagram illustrating the software programs, computer hardware and robot connections of a robot control system according to the present invention.

The invention disclosed herein is, of course, susceptible of embodiment in may different forms. Shown in the drawings and described herein below in detail are preferred embodiments of the invention. It is to be understood, however, that the present disclosure is an exemplification of the principles of the invention and do not limit the invention to the illustrated embodiments.

In the FIGURES, a single block or cell may indicate several individual software and/or hardware components that collectively perform the identified single function. Likewise, a single line may represent several individual signals or several instances of software data sharing or interconnection.

Robots as well as other manufacturing machines include positioning arms with mechanical joints, positioning actuators such as motors for causing movement about the joints, and position feedback sensors which provide an indication of the position of some part of the robot. Automation equipment other than robots generally also include positioning actuators to cause movement about joints, and feedback sensors to provide an indication of the position of parts of the automation equipment.

As used herein, the term "automation equipment" is a reference to the variety of devices used to automate otherwise manual tasks and having mechanical joints for defined motion and mechanical actuators for powering movement about the mechanical joints. Exemplary automation equipment includes industrial robots, laboratory robots, machine tools, parts handlers, laboratory liquid-handling systems, computer media loading systems, therapeutic systems, surgical systems, and the like.

As used herein, the term "mechanical actuator" is a reference to the variety of devices used for robot motion. Exemplary robot actuators are hydraulic pistons, pneumatic pistons, servo motors, stepper motors and linear motors.

As used herein, the term "mechanical actuator" also refers to the variety of devices used to move the joints of automation equipment (or devices). Hydraulic pistons, pneumatic pistons, servo motors, stepper motors and linear motors are equally exemplary of actuators used for the various types of automation equipment other than robots.

Referring to FIG. 1, the elements of a control system 10 are shown with an industrial robot 4, a Cincinnati Milacron 776 robot. Robot 4 includes a series of revolute joints 5, 6, 7 and 8, corresponding servo motors, and an end effector 9. Control system 10 includes a general purpose computer 14 and a real-time computer subsystem 16.

The phrase "general purpose computer," as used herein, refers to commercially available standard computers which are designed for multiple applications as opposed to CPU-based electronics customized for a specific application such as device control. Examples include the well-known group of computers conventionally labeled IBM-compatible personal computers, or more simply PCs. PCs are based on complex instruction set (CISC) CPUs from Intel Corporation (INTEL), Advanced Micro Devices, Inc. (AMD), VIA Technologies, Inc, and the like. The related, evolving CPU product line from INTEL includes CPU chip sets available under the designations "80486®," "Pentium®," "Pentium® II," "Pentium® III." An exemplary CPU product line for general purpose computers by AMD is available under the designation "AMD-K6®." VIA Technologies, Inc. CPUs for general purpose computers are sold under the designation Cyrix®.

General purpose computers based on reduced instruction set (RISC) CPUs are also well known. Examples include computers based on the Alpha® chip set available from the Compaq Computer Corporation.

As indicated in FIG. 1, general purpose computer 14 operates with a general purpose operating system. The phrase "general purpose operating system" is a reference to commercially standard operating systems such as those available from the Microsoft Corp. under the designations MS-DOS®, Windows 95®, Windows 98®, Windows NT®, Windows 2000®, Windows XP®. Other examples of general purpose operating systems include Macintosh® (Apple Computers, Inc.), UNIX (various resellers), OpenVMS® (Compaq Computer Corporation), and the like. The general purpose operating system is preferably a member of the group consisting of a Windows XP®, a Windows-NT®, a Windows 2000®, a Windows 95®, a Windows 98®, an Open VMS®, a PC/MS DOS, and a Unix.

Installed for running on the general purpose computer are a program execution module 18, an operator interface module 20, and watchdog communication code segments 22. The term "module," as used herein refers to a software element such as a program, subprogram, software process, subroutine, or grouping of code segments and the like. The software modules of control system 10 are preferably discrete executable programs which run as discrete processes. Unless otherwise indicated, the software modules and code segments are configured to share access to a variety of software variables and constants as needed through subroutine calls, common shared memory space, and the like.

Program execution module 18 processes programs of robot instructions 24, which can be stored as data files as represented in FIG. 1. From robot instruction programs 24, program execution module 18 generates robot move commands 26 for delivery to real-time computer subsystem 16. Via execution module 18, the relatively more human readable robot instructions 24 generated by a robot operator are interpreted and translated into move commands 26 for real-time computer subsystem 16.

As well, program execution module 18 allows operator control of the running of robot programs 24 by selectively starting and stopping the transfer of move commands 26 to real-time computer subsystem 16 in response to prompts from the operator via operator interface module 20.

Operator interface module 20 is operably linked to an operator display screen 28, a keyboard and/or mouse 30, and other standard peripherals as desired. In a preferred embodiment, display screen 28 is a touch screen which allows a robot operator to input prompts and data through both displays and keyboard/mouse 30.

With robot operator prompts and selections, operator interface module 20 allows robot instruction files 24 to be loaded from disk and processed (or executed) by program execution module 18 for controllably moving robot 4. Operator interface module 20 generates operator screens and accepts from the operator numeric data and prompts. Numeric data entries are communicated to other program modules as necessary.

Prompts by the robot operator to start and stop the running of a robot program are received by operator interface module 20 and forwarded to execution module 18.

In addition to accepting operator inputs for loading, starting and stopping programs 24, operator interface 20 preferably includes an editor for use by an operator to generate new programs of robot instructions 25. Because the present invention provides a control system which relies upon general purpose computers such as a Windows NT PC, it is equally possible to generate robot programs on another PC such as an office PC and then transfer the file to general purpose computer 14 through standard peripherals such as disk drives or computer network connections.

General purpose computer 14 is electronically linked for data exchange (i.e. communication) with real-time computer subsystem 16. Real-time computer subsystem 16 preferably includes a hardware, firmware and software combination designed for process control applications. As opposed to general purpose computers with general purpose operating systems, real-time computers provide for substantially uninterruptible execution of calculations required for a plurality of control loops with relatively fast cycle times (e.g. 0.5-2 msec).

Because of the extensive signal processing requirements, the CPU computer of real-time computer subsystem 16 is preferably a DSP-based computer. In this category of DSP-based control computers, the systems commercially available from Delta Tau Data Systems, Inc. (Chatsworth, Calif.) under the designations "PMAC", "PMAC2," "Turbo PMAC" and "UMAC" are presently preferred.

Real-time computer subsystem 16 includes a robot move module 32, a move command data buffer 34, kinematic models 36, servo control algorithms 38, and watchdog intercommunication code segments 40. Real-time subsystem 16 also includes I/O hardware and software drivers to provide an operable link to the positioning related electronics of robot 4. Represented by block 42 in FIG. 1 are the hardware and software components necessary for receiving and translating robot feedback signals 44 into computer data feedback signals 46. Likewise, block 48 represents the components necessary for converting computer data setpoints 50 into actuator-appropriate activation signals 52.

Activation signals 52 and feedback signals 44 may be analog signals, digital signals or combinations of both depending upon the configuration of robot 4. For example, the typical motor-with-amplifier actuator calls for an analog activation signal. Newer, so-called "smart" devices can be directly activated by digital signals, however. Thus, the type of signal conversion performed by I/O systems 42 and 48 varies by robot configuration.

Robot move module 32 is resident in real-time computer subsystem 16 to accept move commands 26 and feedback signals 44/46 to generate the necessary activation signals 50/52. Robot move module 32 relies upon kinematic models 36 and servo control algorithms 38 to translate move commands 26 into required joint positions and then appropriate activation signal setpoints 50. In a preferred embodiment of the present invention, move commands 26 are expressed as changes in joint position or as changes in end-effector position.

Move commands based on joint position rely upon a predefined range on a one-dimensional joint axis model, for example, +90 degrees to −90 degrees for a revolute axis and 0 to 1200 millimeters (mm) for a linear joint. An example of a move command based on joint position is "set joint one at 60 degrees." In a preferred embodiment of the present invention, robot move module 32 is programmed to accept joint move commands as a function call specifying the position of all robot mechanical joints 5, 6, 7 and 8, thereby allowing only one or all joints to be moved, as desired.

Move commands expressed as end-effector positions rely upon a predefined, but customary, three-dimensional coordinate system for locating the end-effector. A move command based on end-effector position is a call to move the end effector to a point in the end-effector's workspace.

For joint position move commands, robot move module 32 includes software models for translating data from feedback signals 46 into joint position. The required calculation varies according to joint type and the type feedback signal available. For example, a feedback sensor directly measuring an indication of joint position requires limited translation, while a feedback sensor measuring the number of rotations of a positioning motor may require a more complex translation.

To process move commands based on end-effector position, robot move module 32 additionally includes a kinematic model for calculating the required position of joints 5, 6, 7 and 8, given a desired position for end effector 9.

More specifically, real-time computer subsystem 16 uses kinematic model algorithms for computation of the forward and inverse kinematics of the robot. Forward kinematics computation refers to the determination of end-effector position and orientation given known joint positions or actuator positions of the robot. Inverse kinematics is the determination of the joint angle or actuator positions given an end-effector position.

The required combination of individual joint axes models and overall kinematics models is represented in FIG. 1 by block 36.

Kinematic algorithms are described in other patents and the technical literature. See, for example, Chapters 3 and 4 of Craig, John J. *Introduction to Robotics: Mechanics and Control*, 2nd Ed., Addison-Wesley, 1989. The specific models employed vary according to the electromechanical configuration of the robot to be controlled.

Because the positioning actuator and feedback sensor combination make up a dynamic system, real-time computer subsystem 16 also includes control algorithms 38 to provide the required dynamic calculations. Preferred among available closed loop servo motor control schemes is a proportional-integral-derivative (PID) with feedforward algorithm.

Data buffer 34 is a software variable available to programs in both general purpose computer 14 and real-time computer subsystem 16 for storing multiple move commands 26 received from program execution module 18. Although the desired storage capacity for data buffer 34 can vary, in a preferred embodiment of the present invention data buffer 34 and connected modules are preferably configured such that from 2 to 10, and more preferably from 3 to 4, move commands are stored.

With move command data buffer 34, control system 10 provides for substantially continuous, uninterrupted control of robot 4 even in response to program execution delays in general purpose computer 14.

As noted above, general purpose computers running general purpose operating systems are relatively unreliable, exhibiting unpredictable control program interruption. Specific motion control of robot 4 by real-time computer subsystem 16 is not affected by unpredictable delays in operations of general purpose computer 14 because robot move module 32 can continue to draw move commands 26 from data buffer 34.

Although a variety of data transfer mechanisms are available to provide electronic and software-level communication between general purpose computer 14 and real-time computer subsystem 16, a commercially standard data bus backplane is preferred. The data bus connection is symbolically represented in FIG. 1 by reference numeral 54. Suitable data bus standards can be selected from the group consisting of an ISA bus, a PCI bus, a VME bus, a universal-serial-bus (USB), an Ethernet connection, and the like. The ISA bus, the PCI bus, and the VME bus are exemplary standard data buses, with the ISA bus being presently preferred.

For convenient space-saving connection to data bus 54, the computer mother board portions of general purpose computer 14 and real-time computer subsystem 16 are data bus cards. As used herein, the term "bus card" is a reference to printed circuit boards with electronic components and a tab with a plurality of contacts that is received in the card slots of a data bus chassis. The DSP real-time computers available from Delta Tau Data Systems, Inc. noted above are available as ISA data bus cards.

Figure 2:
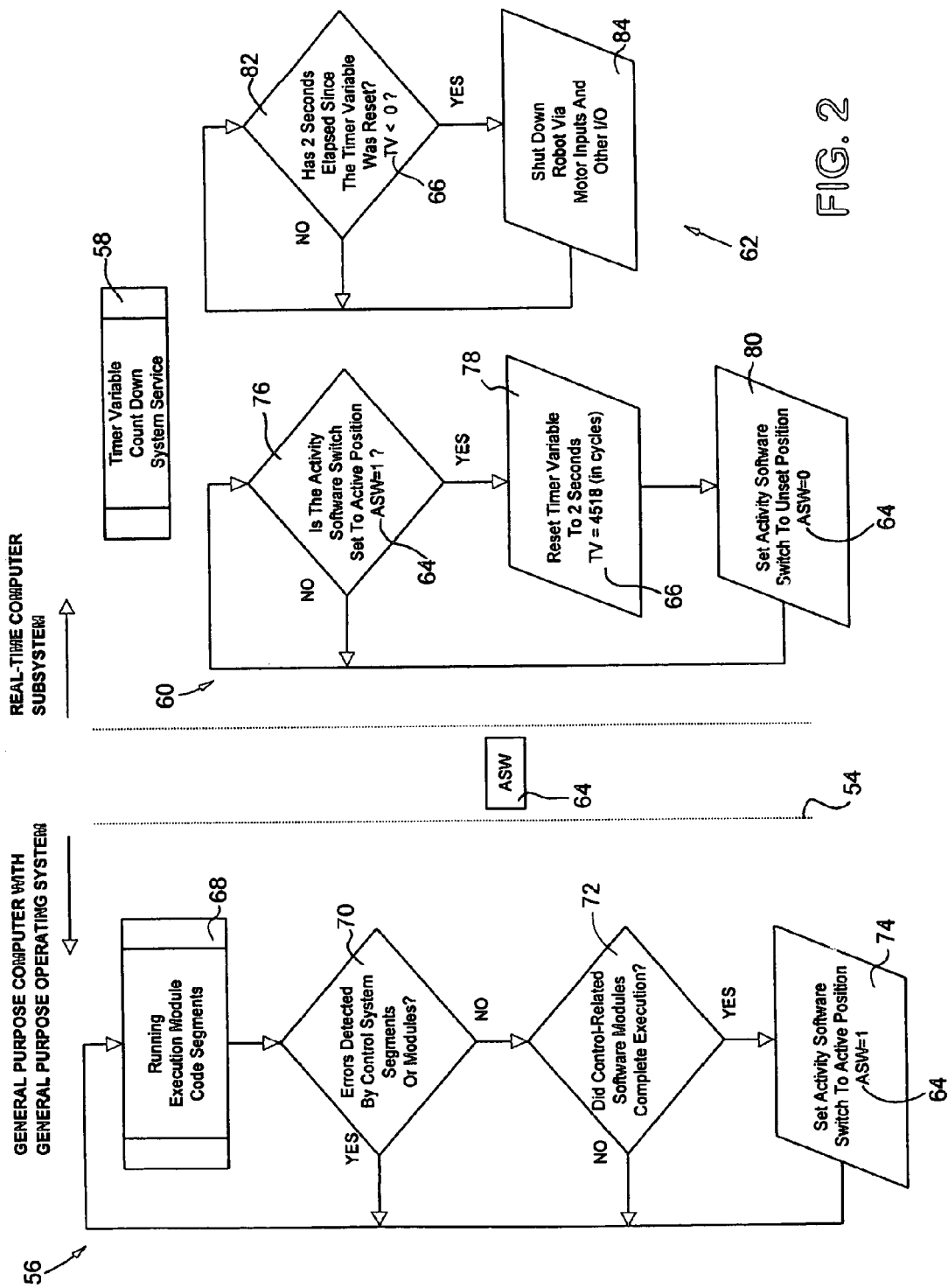
FIG. 2 is simplified flowchart of a preferred embodiment of software and method steps for providing a watchdog intercommunication between the general purpose computer and the real-time computer subsystem.

In a preferred embodiment, control system 10 includes a security (or "watchdog") communication (blocks 22 and 40) between general purpose computer 14 and real-time computer subsystem 16. Flowchart FIG. 2 shows the preferred code segments for maintaining the watchdog management. As illustrated, a preferred watchdog scheme includes code segments operating in both general purpose computer 14 and real-time computer subsystem 16. Resident in general purpose computer 14 is a status code segment 56 and resident in the real-time computer subsystem are a timer code segment 58, a timer reset code segment 60, and a fail safe code segment 62.

The code segments interact with two software variables: an activity software switch (ASW) 64 for indicating whether programs in general purpose computer 14 are active and/or error free, and a timer variable (TV) 66 for storing an elapsed time indication. Timer variable 66 is resident in real-time computer subsystem 16 while activity software switch (ASW) 64 is shared via data bus 54 or other means. Activity software switch 64 is implemented as an integer software variable with an unset position being represented by zero and a set, or active position, being represented by one.

Status code segment 56 optionally, but preferably, runs sequentially with program execution module 18 (box 68) and repeatedly sets activity software switch 64 to the active position (box 74). After the completion of a run cycle of program execution module 18, status code segment 56 examines other software variables which indicate special errors (box 70) or delays in the processing of other programs (box 72) in the general purpose computer 14. Accordingly, if program execution module 18 is interrupted or if errors or other delays are detected, activity switch 64 is not set.

Timer code segment 58 counts down timer variable 66 according to elapsing time. Timer code segment 58 is preferably a system service function of real-time computer subsystem 16 and expressed in execution cycles.

When the activity software switch is in the active position (box 76), timer reset code segment 60 repeatedly resets the timer variable to a predetermined amount of time (box 78; preferably two seconds) and repeatedly sets the activity software switch back to the unset position (box 80). Fail safe code segment 62 responds to an overrun of timer variable 66 (box 82) by shutting down robot 4 via activation signals 50/52 and other robot I/O.

Acting together, code segments 56, 58, 60 and 62, provide a watchdog service which will shut down robot 4 if the operation of general purpose computer 14 is stopped or delayed for more than two seconds.

Referring back to FIG. 1, another feature of the present invention is that the software provided for general purpose computer 14 is suitable for controlling robots of various electromechanical configurations. According to this aspect of the invention, general purpose computer 14 serves as a robot-independent computer unit while real-time computer subsystem 16 serves as a somewhat robot-specific controller unit, or customized interface or adapter to the robot.

Figure 3:
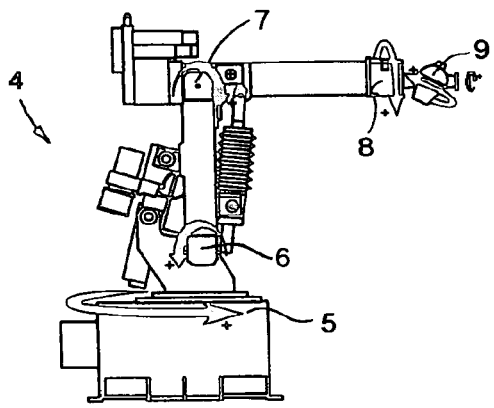
FIG. 3 is a side elevation view of an articulating industrial robot illustrating another type of robot configuration controllable by embodiments of the present invention.
Figure 4:
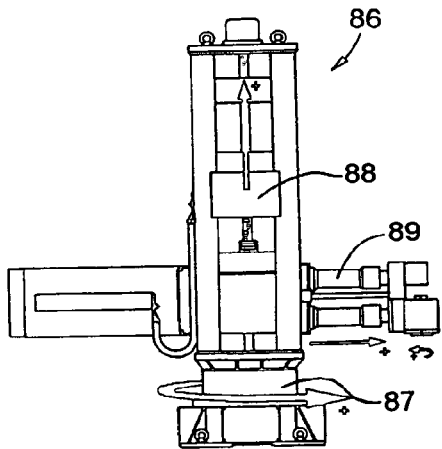
FIG. 4 is a side elevation view of an industrial robot equipped with linear joints and illustrating one of the many types of robot configurations controllable by embodiments of the present invention.

Important to the multi-configuration aspect of the present invention is the enhanced versatility of operator interface module 20. Viewed together, FIGS. 3 and 4 demonstrate the challenge of working with robots of different electromechanical configurations. FIG. 3 is side view of articulating robot 4 from FIG. 1 in slightly larger scale to reveal greater detail. The arms of robot 4 are connected by a series of revolute (or rotary) joints 5, 6, 7 and 8. In contrast, FIG. 4 is side view of a robot 86 which is equipped with a revolute, torso joint 87 and two linear joints 88 and 89.

Assigning joint numbers from the base up, the second and third joints of robot 4 are of a different type than the second and third joints of robot 86. To overcome this difference in configuration, the operator interface of the present invention includes a configuration variable for storing data specifying the electromechanical configuration of the robot and display generating code segments for each type of configuration.

In a preferred embodiment, the configuration variable is defined and/or sized to store data defining the type of robot joint, linear or revolute, and whether a specified revolute joint is windable, i.e. capable of turning more than 360 degrees.

Figure 5:
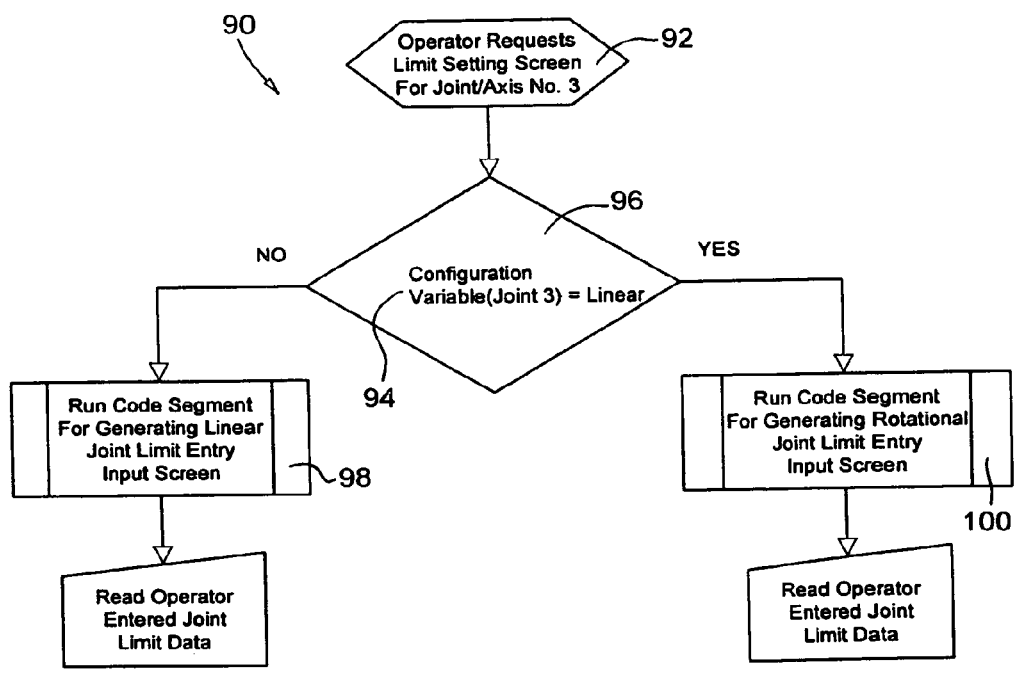
FIG. 5 is a simplified flow chart of preferred software and method steps for accommodating robots of different electromechanical configurations and demonstrating the role of the configuration variable in control systems according to the present invention.
Figure 6:
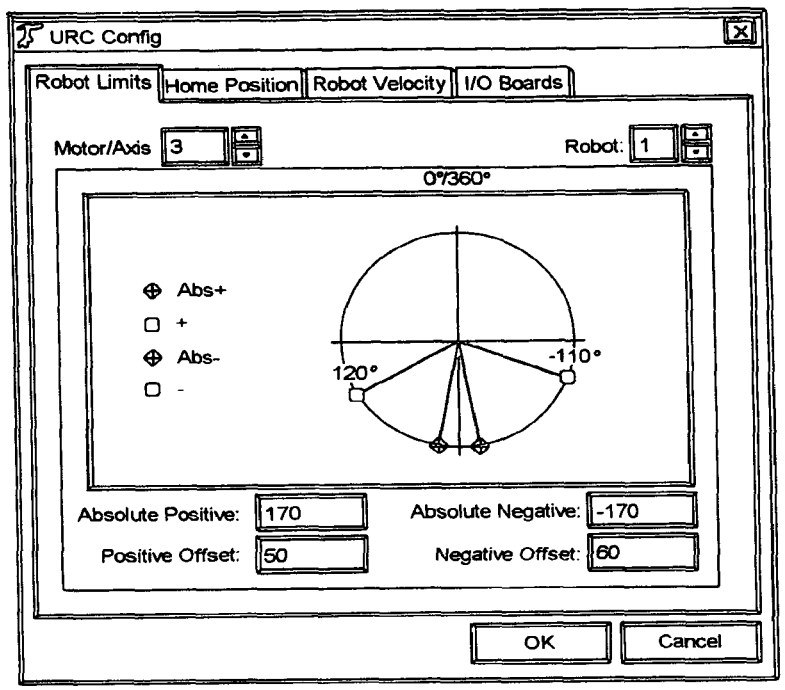
FIG. 6 is likewise an exemplary operator interface display screen generated in response to data stored in the configuration variable specifying a rotational joint configuration.
Figure 7:
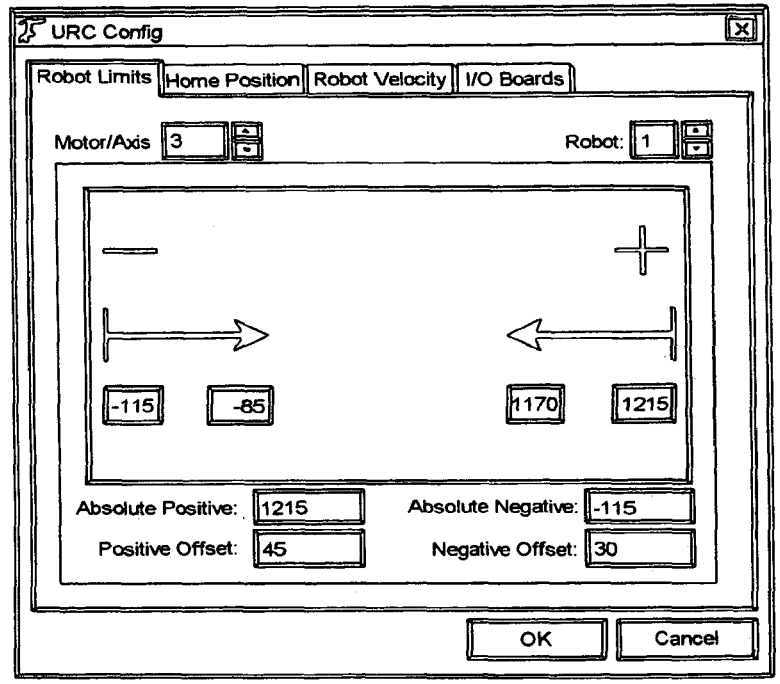
FIG. 7 is an exemplary operator interface display screen generated in response to data stored in the configuration variable specifying a linear joint.

FIGS. 5 through 7 provide an example of how operator interface module 20 (FIG. 1) uses the configuration variable to accommodate different types of robots. As illustrated in FIG. 5, a display selecting code segment 90 responds to an operator request to set limits for joint/axis 3 (box 92). Code segment 90 checks in configuration variable 94 for data specifying whether joint 3 is linear or revolute (box 96).

Depending upon whether the third joint of the robot to be controlled is revolute as with robot 4 or linear as with robot 86, code segment 90 selects one of two available displays for setting joint limits. For a revolute joint type, box 98 is selected and the revolute joint/axis display of FIG. 6 is generated at screen 28. For a linear joint type, box 100 is selected and the linear joint/axis display of FIG. 7 is generated.

Operator interface module 20 is one example of the many software processes installed on general purpose computer 14 that preferably rely on settings in an electromechanical configuration variable (i.e. data set) to provide adaptability. An exemplary configuration variable is defined to store specifications for the number of mechanical joints present on the robot or other automation equipment to be controlled, the type for each joint (e.g. linear), the distance between respective mechanical joints and the range of motion for each joint.

Figure 8:
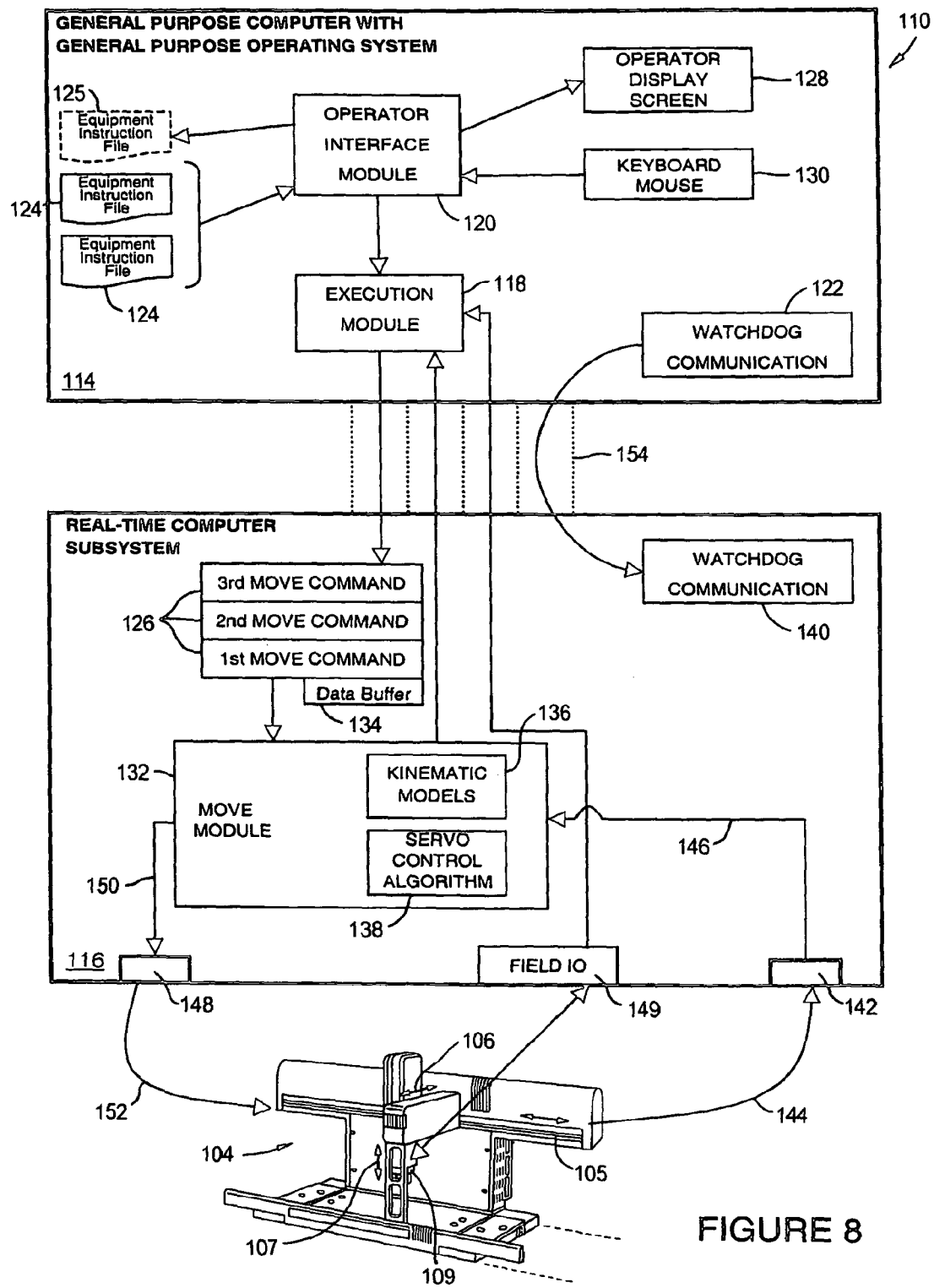
FIG. 8 is schematic block diagram illustrating the software programs, computer hardware and equipment connections of an automation equipment control system according to the present invention applied to a laboratory liquid-handling system.

FIG. 8 illustrates a control system 110 according to the present invention applied to laboratory automation equipment, and more specifically, a laboratory liquid handling system 104. Liquid handling system 104 has three linear mechanical joints 105, 106 and 107, corresponding servo motors and a pipette end effector 109. End effector 109 preferably includes an optical detector in the form of a digital camera for providing control system 110 an alignment indicator.

Control system 110 includes a general purpose computer 114 and a real-time computer subsystem 116. Installed on the general purpose computer are a program execution module 118, an operator interface module 120, and watchdog communication code segments 122.

Program execution module 118 is a software process adapted to processes automation equipment instructions 124. As noted above in reference to robot control system 10 (FIG. 1), the instructions 124 are preferably stored as data disk files on general purpose computer 114 or on compatible removable storage media. From equipment instruction programs 124, program execution module 118 generates move commands 126 for delivery to real-time computer subsystem 116.

Equipment instructions 124 preferably take the form of operator readable text or flow-chart source code. Execution module 118 translates equipment instructions 124 into move commands 126. Via operator interface module 120, program execution module 118 allows equipment operators to start and stop the transfer of move commands 126 to real-time computer subsystem 116.

Operator interface module 120 is operably linked to an operator display screen 128, a keyboard and/or mouse 130, and other standard peripherals as desired. Interface module 120 includes code segments to create operator screens and accept operator inputs. Interface module 120 allows robot instruction files 124 to be loaded from disk and processed by program execution module 118 for controllably moving liquid handling system 104.

In addition to accepting operator inputs for the loading, starting and stopping of programs 124, operator interface 120 includes a file editor for use by an operator to generate new instruction files 125.

General purpose computer 114 is electronically interconnected for data communication with real-time computer subsystem 116 via one of a variety of a standard data buses 154 as described above in reference to control system 10. A preferred real-time computer for providing subsystem 116 is commercially available from Galil Motion Control (Rocklin, Calif.) under the designation "DMC-18x2." The DMC-18x2 real-time computers rely on a PCI bus connection to general computer 114.

Real-time computer subsystem 116 includes a move module 132, a move command data buffer 134, kinematic models 136, servo control algorithms 138, and watchdog intercommunication code segments 140. Subsystem 116 also includes I/O hardware and software drivers to provide an operable link to the positioning related electronics of liquid handling system 104. Represented by block 142 are the hardware and software components necessary for receiving and translating liquid handling system feedback signals 144 into computer data feedback signals 146. Block 148 represents the components necessary for converting computer data setpoints 150 into actuator-appropriate activation signals 152.

Laboratory liquid handling system 104 is equipped with a pipette end effector 109 including control valves, a peristalic pump and optionally a flow rate sensor. Block 149 represents the hardware and software interface components for accessing these end effector elements.

Move module 132 accepts move commands 126 and feedback signals 144/146 to generate the necessary activation signals 150/152. Move module 132 relies upon kinematic models 136 to translate move commands 126 into required joint positions and then appropriate activation signal setpoints 150. Move commands 126 may be specified as changes in joint position or as changes in end-effector position.

For example, to process move commands based on the position of pipette 109, move module 132 includes a kinematic model for calculating the required position of joints 105, 106 and 109.

Data buffer 134 is a software variable available to programs in both general purpose computer 114 and real-time computer subsystem 116 for storing multiple move commands 126 generated by program execution module 118. Data buffer 134 preferably includes capacity to store from 2 to 10, and more preferably from 3 to 4, move commands.

Figure 9:
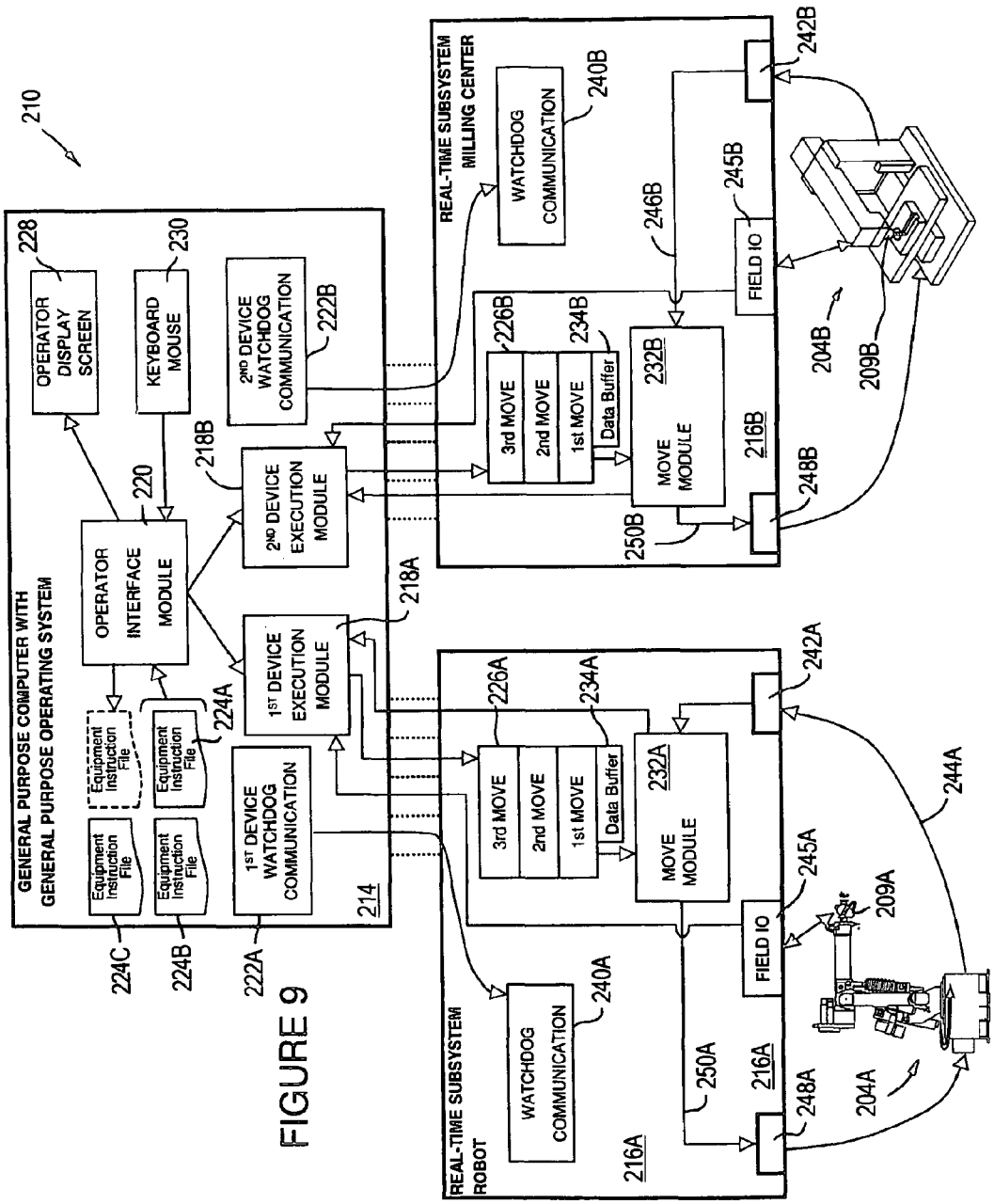
FIG. 9 is schematic block diagram illustrating a control system according to the present invention applied to simultaneously control two different automation equipment centers.

Also contemplated for the present control systems is the operator direction of multiple automation devices via a single general-purpose computer. Referring now to FIG. 9, system 210 simultaneously controls both an industrial robot 204A and a multi-axis milling machine tool 204B.

As described above in reference to robot 4 and control system 10 (FIG. 1), robot 204A is a Cincinnati Milacron 776 robot having a series of revolute mechanical joints, corresponding servo motors and an end effector 209A. Milling machine tool 204B is equipped with a series of orthogonally disposed linear mechanical joints with conventional actuators and a cutting tool end effector 209B.

Each automation device 204A and 204B is served by separate real-time computer subsystems 216A and 216B, respectively. Real-time subsystem 216A is customized for control of robot 204A. Subsystem 216A includes hardware and software interface components 248A to transfer activation signal setpoints 250A to robot 204A actuators, interface components 242A to receive and translate position feedback signals 244A and interface components 245A for communication with end effector 209A. Also installed on real-time subsystem 216A is a move command data buffer 234A for receiving move commands 226A from general purpose computer 214, a move module software process 232A for translating move commands into activation signal setpoints 250A and watchdog communication code segments 240A to shutdown robot 204A in the event of a fault in general purpose computer 214.

Subsystem 216B is customized for control of the relatively less complex milling center 204B. Subsystem 216B includes software and hardware components corresponding to those identified for subsystem 216A, namely, a move data buffer 234B for storing move commands 226B, a move module 232B for processing move commands 226B into activation signal setpoints 250B, watchdog code segments 240B, interface components 248B for generating activation signals 252B, interface components 245B for directing end effector 209B and interface components 242B for translating feedback signals 244B into digital software data 246B.

It is a feature of the present invention that the interface hardware (e.g. 245A/B and 248A/B) and the software modules making up the real-time subsystems can be customized according to the selected automation equipment to be controlled, while the software modules resident on the general purpose computer (e.g. operator interface 220) can accommodate differing automation devices and their related electromechanical configurations. For example, industrial robot 204A has at least four revolute mechanical joints and corresponding actuators, while machining center 204B has a lower number of linear joints. Therefore, milling center subsystem 216B is customized with relatively less complex interface connections, than the connections required by subsystem 216A for robot 204A. Furthermore, the kinematic model present in move module 232B of subsystem 216B for machining center 204B can be relatively less complex than those kinematic models present in move module 232A of subsystem 216A.

General purpose computer 214 of control system 210 has an operator interface 220 linked to a display 228 and peripherals 230, and separate execution modules 218A and 218B for each automation device subsystem. Operator interface module 220 generates operator screens and accepts from the operator, prompts and data.

Operator interface module 220 allows the creation and loading of equipment instruction programs, which are represented in FIG. 9 with reference numerals 224A, 224B and 224C. More specifically, 224A represents files with instructions solely for robot 204A, 224B represents files with instructions solely for milling center 204B, 204C represents files containing instructions for both robot 204A and milling center 204B.

FIG. 9 represents a single operator interface module 220 for directing the activities of both automation devices, robot 204A and milling center 204B. In an alternate embodiment, general purpose computer 214 includes a separate operator interface module for each automation device.

Execution module 218A processes programs of instructions for robot 204A and stores corresponding move commands 226A in data buffer 234A. Execution module 218B translates instruction programs 224 for milling center 204B storing resulting move commands 226B to data buffer 234B.

In an alternate embodiment, control system 210 relies on a single execution module to translate instructions for multiple automation devices and selectively forward move commands 226A or 226B to the appropriate subsystem.

Although represented in FIG. 9 as two separate blocks 222A and 222B, the watch dog intercommunication function between general purpose computer 214 and each real-time subsystem 216A and 216B preferably relies on the same operating code segments. The watchdog code segments in general purpose computer 214 set separate activity software switches for each subsystem 216A and 216B. If one or more critical software processes fail to execute, neither the activity software switch for subsystem 216A nor the activity software switch for subsystem 216B will be set to active. As described above in reference to FIG. 2, if the activity software switches are not set to active in a timely manner, the watchdog code segments 240A and 240B operating in each real-time subsystem will shut down their respective automation devices.

Figure 10:
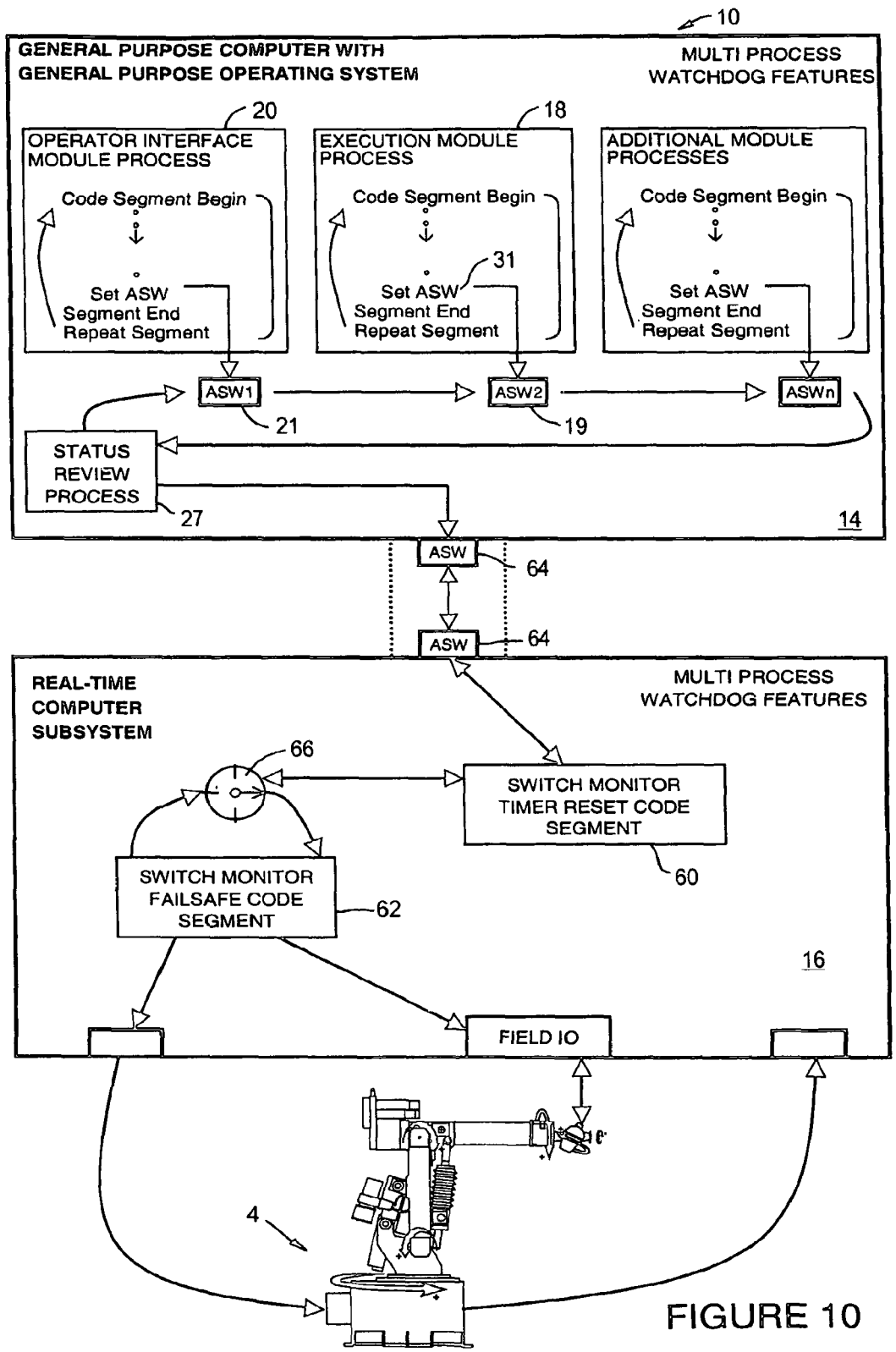
FIG. 10 is a schematic block diagram showing features of the watchdog intercommunication applied to multiple processes in the general purpose computer.

A key feature of the present invention is the watchdog intercommunication between the general purpose computer and the real-time computer subsystem. FIG. 10 illustrates a preferred embodiment of the watchdog intercommunication feature applied individually to multiple software processes of control system 10.

Control system 10 includes multiple software processes, some of which are critical to the control function such as execution module 18 and operator interface 20. According to a preferred approach to the watchdog feature, control system 10 includes an activity software switch for each critical process. For example, execution module 18 has an activity software switch 19 (ASW1) and operator interface module 20 has an activity software switch 21 (ASW2). A separate high-priority, status review process 27 polls the plurality of activity software switches, ASW1 . . . ASWn, and sets a main activity software switch 64 (ASW) only if all of the individual process activity switches are active.

Each critical software process has code segments for setting the assigned activity software switch to active. For example, execution module 18 includes code segment 31. This activity code segment is preferably at the end of the execution sequence. If a critical process fails to fully execute, the activity software switch is not set and subsystem 16 fails safe to shutdown robot 4.

Timer reset code segment 60 in real-time subsystem 16 continually resets timer variable 66 when main software activity switch 64 is set to the active position. A system-service timer code segment 58 (FIG. 2) continually increments timer variable 66 according to elapsed time. Timer variable 66 therefore serves as a measure of elapsed time since software processes of general purpose computer reported activity. Fail safe code segment 62 monitors timer variable 66 and shuts down robot 4 if the elapsed time of inactivity exceeds a predetermined safety limit.

The foregoing specification and drawings are to be taken as illustrative but not limiting of the present invention. Still other configurations and embodiments utilizing the spirit and scope of the present invention are possible, and will readily present themselves to those skilled in the art.

I claim:

1. A control system comprising:
a general purpose computer with a general purpose operating system, said general purpose computer including a program execution module configured to selectively start and stop processing of the at least one program of instructions for mechanisms having: at least one mechanical joint; a mechanical actuator to move the at least one mechanical joint; and a position feedback sensor;
a real-time computer subsystem configured to be in electronic communication with said general purpose computer and configured to link to the mechanical actuator and the position feedback sensor;
a move command data buffer configured to store a plurality of move commands;
a mechanism move module configured to: link to said move command data buffer; sequentially process said plurality of move commands; and calculate a target position for the at least one mechanical joint; and
a control algorithm component configured to communicate with said mechanism move module to calculate an activation signal; the activation signal calculated from a position signal and said target position for the at least one mechanical joint, the activation signal configured to actuate the mechanical actuator.

2. The control system according to claim 1 further comprising a watchdog intercommunication module configured to enable intercommunication between said real-time computer subsystem and said general purpose computer to detect faults in operation of said general purpose computer.

3. The control system according to claim 2 wherein said watchdog intercommunication module includes:
a timer variable for storing an elapsed time indication;
a timer code segment configured to adjust said timer variable according to passing time;
an activity software switch having an active position and an unset position;
a status code segment installed in said general purpose computer configured to repeatedly set said activity software switch to said active position;
a timer reset code segment installed in said real-time computer subsystem configured to repeatedly reset said timer variable to a predetermined amount of time when said activity software switch is in said active position and repeatedly set said activity software switch to said unset position; or
a fail safe code segment installed in said real-time computer subsystem configured to repeatedly inspect said timer variable and, if said timer variable reaches a predetermined value, set said activation signal to shut down the mechanisms.

4. The control system according to claim 3 wherein said activity software switch is implemented as an integer software variable with said unset position being represented by zero and said active position being represented by one.

5. The control system according to claim 1 further comprising a data bus configured to receive bus cards and wherein said real-time computer subsystem includes a bus card with a central processing unit, said bus card being installed in said data bus.

6. A control system configured to control a plurality of automation devices, each automation device having a mechanical joint and a mechanical actuator to move the mechanical joint, the control system comprising:
  a general purpose computer with a general purpose operating system, the general purpose computer including a first digital processor configured to run an operator interface module; and
  at least one real-time computer subsystem configured to communicate electronically with said general purpose computer and link to one of said automation devices, the at least one real-time computer subsystem, including a digital processor, configured to run a real-time tied operating system and a move module for executing a plurality of move commands.

7. A control system of claim 6 configured to control a series of complex mechanisms.

8. The control system according to claim 6 further comprising a watchdog intercommunication module configured to enable intercommunication between at least one of said plurality of real-time computer subsystems and said general purpose computer to detect faults in operation of said general purpose computer.

9. A control system according to claim 6 wherein the at least one real-time computer subsystem includes:
  a move command data buffer configured to store said plurality of move commands;
  a move module configured to: link to said data buffer; sequentially process said plurality of move commands; and calculate a target position for the mechanical joint; and
  a control algorithm component configured to communicate with said move module to calculate an activation signal; the activation signal calculated from said target position for the mechanical joint.

10. A control system comprising:
  an equipment independent computer including one or more modules configured to generate a plurality of move commands for operating mechanical equipment, the mechanical equipment having: at least one mechanical joint; a mechanical actuator configured to move the at least one mechanical joint; and a position feedback sensor;
  a move command data buffer configured to store the plurality of move commands; and
  an equipment-specific controller configured to:
    communicably link to the equipment independent computer, the mechanical actuator, and the position feedback sensor;
    sequentially process the plurality of move commands from the move command data buffer to calculate a desired position for the mechanical joint;
    determine a current position of the mechanical joint based on a position signal received from the position feedback sensor; and
    calculate an activation signal to actuate the mechanical actuator based on the desired position and the current position.

11. A control system as recited in claim 10, wherein the equipment specific controller is a digital signal processor.

12. A control system as recited in claim 10, wherein the move command data buffer is provided as a component of the equipment-specific controller.

13. An equipment-specific controller device comprising:
  a digital signal processor (DSP);
  a move command buffer accessible to the DSP and to an equipment-independent computing device, the move command buffer configured to store a plurality of move commands, the move commands generated by the equipment-independent computing device to operate automation equipment; and
  one or more modules executable by the DSP, the modules configured to:
    sequentially process the move commands from the move command buffer; and
    operate the automation equipment in a continuous manner including continued operation of the automation equipment during an interruption of the equipment-independent computing device.

14. The equipment-specific controller device of claim 13, wherein the one or more modules are further executable by the digital signal processor to:
  calculate specified positions for mechanical joints of the automation equipment based on the move commands generated by the equipment-independent computing device;
  determine current positions of the mechanical joints based upon one or more feedback signals received from the automation equipment; and
  generate one or more activation signals to cause operation of the mechanical joints based upon the current positions and the specified positions.

15. The equipment-specific controller device of claim 14, wherein the one or more activation signals cause operation of one or more actuators to operate corresponding joints of the automation equipment.

16. The equipment-specific controller device of claim 13, wherein one or more move commands stored in the move command buffer is configurable.

17. One or more computer-readable storage media storing instructions that, in response to being executed by a computing device, cause the computing device to perform operations comprising:
  drawing move commands to operate automation equipment of different electromechanical configurations from a move command buffer of the computing device, the move commands being generated for the automation equipment using an equipment-independent computing device; and
  executing the move commands in sequential order to cause operation of the automation equipment, the executing performed using the move command buffer to enable continued operation of the automation equipment during an interruption of the equipment-independent computing device.

18. One or more computer-readable storage media as recited in claim 17, wherein executing the move commands comprises generating activation signals based on the move commands to cause actuators of the automation equipment to move to positions specified by the move commands.

19. One or more computer-readable storage media as recited in claim 17, wherein executing the move commands further comprises communicating the activation signals to the automation equipment to cause corresponding movements.

* * * * *

UNITED STATES PATENT AND TRADEMARK OFFICE
CERTIFICATE OF CORRECTION

PATENT NO. : 8,473,202 B2
APPLICATION NO. : 13/244085
DATED : June 25, 2013
INVENTOR(S) : Lapham It is certified that error appears in the above-identified patent and that said Letters Patent is hereby corrected as shown below:

On the Title Page, in Column 1, under "Related U.S. Application Data", Line 1, delete item "(60)" and insert item -- (62) --, therefor.

On the Title Page, in item (57), under "ABSTRACT", in Column 2, Line 1, delete "A" and insert -- An --, therefor.

In the Specification

In Column 2, Line 9, delete "110" and insert -- I/O --, therefor.

In Column 4, Line 42, delete "same," and insert -- same: --, therefor.

In Column 4, Line 43, delete "is schematic" and insert -- is a schematic --, therefor.

In Column 4, Line 46, delete "is simplified" and insert -- is a simplified --, therefor.

In Column 5, Line 1, delete "is schematic" and insert -- is a schematic --, therefor.

In Column 5, Line 6, delete "is schematic" and insert -- is a schematic --, therefor.

In Column 5, Line 14, delete "DESCRIPTION" and insert -- DETAILED DESCRIPTION --, therefor.

In Column 5, Line 18, delete "may" and insert -- many --, therefor.

In Column 11, Line 50, delete "peristalic" and insert -- peristaltic --, therefor.

In the Claims

In Column 15, Line 20, in Claim 7, delete "A" and insert -- The --, therefor.

Signed and Sealed this
First Day of April, 2014

Michelle K. Lee
*Deputy Director of the United States Patent and Trademark Office*

In Column 15, Line 28, in Claim 9, delete "A" and insert -- The --, therefor.

In Column 15, Line 63, in Claim 11, delete "A" and insert -- The --, therefor.

In Column 16, Line 1, in Claim 12, delete "A" and insert -- The --, therefor.